(12) United States Patent
Vedrine

(10) Patent No.: US 7,618,401 B2
(45) Date of Patent: Nov. 17, 2009

(54) DEVICE FOR INJECTING A PRODUCT, IN PARTICULAR FOR MEDICAL USE

(75) Inventor: Lionel Vedrine, Ridgewood, NJ (US)

(73) Assignee: Becton Dickinson France, S.A.S., Le Pont de Claix (FR)

( * ) Notice: Subject to any disclaimer, the term of this patent is extended or adjusted under 35 U.S.C. 154(b) by 101 days.

(21) Appl. No.: 10/520,981

(22) PCT Filed: Jul. 16, 2003

(86) PCT No.: PCT/FR03/02252

§ 371 (c)(1),
(2), (4) Date: Aug. 29, 2005

(87) PCT Pub. No.: WO2004/009164

PCT Pub. Date: Jan. 29, 2004

(65) Prior Publication Data

US 2006/0111674 A1 May 25, 2006

(30) Foreign Application Priority Data

Jul. 19, 2002 (FR) .................................. 02 09238

(51) Int. Cl.
*A61M 5/00* (2006.01)
(52) U.S. Cl. .................. 604/187; 604/236; 604/256; 604/90
(58) Field of Classification Search .................. 604/90, 604/110, 187, 200–203, 231, 232, 236, 237, 604/244, 247, 256
See application file for complete search history.

(56) References Cited

U.S. PATENT DOCUMENTS

| 4,929,230 | A | * | 5/1990 | Pfleger ........................ 604/90 |
| 5,320,606 | A | | 6/1994 | Jore |
| 6,123,688 | A | * | 9/2000 | Botich et al. ................ 604/220 |
| 6,569,115 | B1 | * | 5/2003 | Barker et al. ................ 604/110 |
| 6,981,963 | B2 | * | 1/2006 | Barker et al. .................. 604/90 |

FOREIGN PATENT DOCUMENTS

| FR | 2 750 051 A | | 12/1997 |
| FR | 2750051 A1 | * | 12/1997 |
| WO | WO 98/13077 A | | 4/1998 |
| WO | WO 99/47194 A | | 9/1999 |
| WO | WO 01/45776 A | | 6/2001 |

* cited by examiner

*Primary Examiner*—Kevin C Sirmons
*Assistant Examiner*—Bhisma Mehta
(74) *Attorney, Agent, or Firm*—David M. Fortunato; Hoffmann & Baron LLP

(57) ABSTRACT

This device comprises:
a body housing a hollow injection needle and a container containing the injectable product; the needle is connected to the body but able to move relative to the latter between an injection position and a retracted position;
a plunger that slides in the body and is displaceable relative to the latter to perform the injection; the container is able to move relative to the plunger between a position that enables the injection to be performed and a retracted position;
an arrangement for keeping the needle and the plunger in injection position, which arrangement can be released to free the needle and the plunger to move to the retracted position.

4 Claims, 7 Drawing Sheets

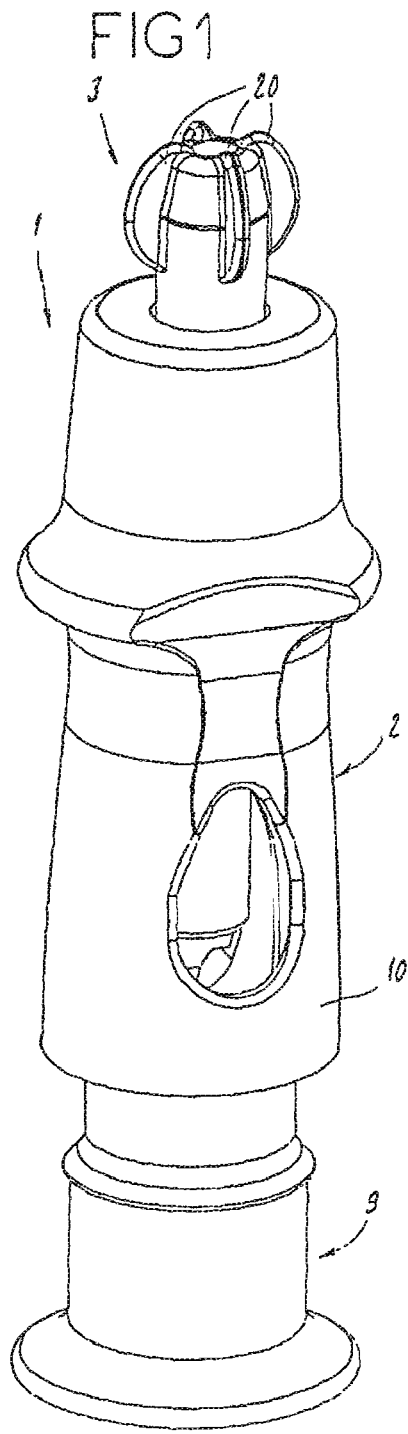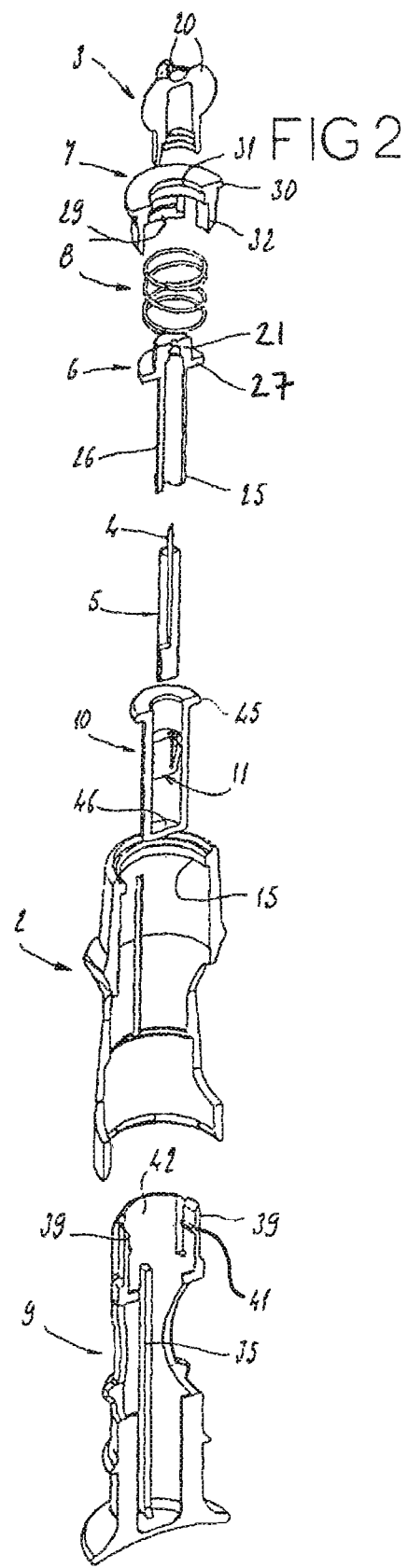

DEVICE FOR INJECTING A PRODUCT, IN PARTICULAR FOR MEDICAL USE

BACKGROUND OF THE INVENTION

The present invention relates to a device for injecting a product, particularly for medical use. This device is particularly designed for performing an intradermal injection.

In the following description, the terms "proximal" and "distal" are considered with reference to the direction in which the product is injected.

DESCRIPTION OF THE PRIOR ART

Intradermal injections are often performed with conventional syringes, the needle being inserted at a direction forming a slight angle with the skin.

These conventional syringes do not inject completely reliably, nor are they totally proof against the risk of accidental stabs which can occur after the injection.

The invention seeks to overcome this fundamental problem.

The object of the invention is therefore to provide a device that injects with complete reliability and is totally proof against the risk of accidental stabbing.

SUMMARY OF THE INVENTION

This object is achieved with a device comprising:
- a body housing an injection needle and a container containing the injectable product; the needle is connected to the body but able to move relative to the latter between an injection position and a retracted position;
- a plunger that slides in the body and is displaceable relative to the latter to perform the injection; said container is closed at one end and is connected to this plunger but is able to move relative to the latter between a position that enables the injection to be performed and a retracted position;
- means for keeping the needle in position, which means normally keep the needle in the injection position and can be released to free the needle to move to said retracted position;
- means for keeping the container in position, which means normally keep the container in the position that enables the injection to be performed, and can be released to free the container to move to said retracted position;
- a piston engaged in the container and so shaped that, in a first configuration of the piston or relative position of this piston and of this container, it closes the container in such a way as to isolate the product from the environment outside this container and, in a second configuration of the piston or relative position of this piston and of this container, it allows the product to pass out of the container, and
- respective means for operating said means of holding the needle in position and said means of holding the container in position, which, at the end of the injection, release the means of holding the needle in position before, or at the same time as, said means of holding the container in position are released.

While the injection is being performed, the needle is kept in the injection position relative to the body and the container is kept in the injection position relative to the plunger. The movement of the plunger relative to the body whereby the closed end of the container is moved toward the needle moves the piston into said second configuration or position, allowing the product to pass out of the container.

At the end of the injection, the respective operating means release said means of keeping the needle in position and said means of keeping the container in position. This allows the needle and container to be moved into the retracted position. This retraction makes the device totally proof against the risk of accidental stabbing.

The piston may be so shaped that, in said second configuration or position, it allows the product to pass between itself and the container. The piston may in particular comprise at least one peripheral zone that is able, in said first configuration of the piston, to press tightly against the wall of the container, and, in said second configuration of the piston, to withdraw under the pressure of the injectable product to allow the latter to pass it.

The piston may also comprise a pierceable zone located in line with the proximal end of the needle. The movement of the container relative to the needle thus causes the proximal end of the needle to pierce this pierceable zone of the piston so that it comes into communication with the injectable product and allows this product to flow out through the needle.

Advantageously, the device comprises spring means for moving the needle and the container to the retracted position without voluntary external action.

Advantageously, said body forms a distal wall perpendicular to the axis of the needle, from which the needle projects, in the injection position, to a distance equal to the desired depth of insertion of this needle during the injection.

This distal wall forms a stop wall designed to be pressed against the skin when the needle is inserted in order to limit its insertion to said desired depth.

The device according to the invention is thus particularly suitable for performing intradermal injections.

In the retracted position, the needle can be simply retracted behind this wall, in the proximal direction, to eliminate the risk of accidental stabbing after injection.

In one possible embodiment of the invention, said means of holding the needle in position comprise:
- a needle-supporting part comprising at least one locking means; and
- at least one tab that comprises a locking means able to engage with that of said needle-supporting part, this tab being moveable radially between a normal, radially inward position, in which said locking means engage with each other to keep said needle-supporting part in position relative to said body, and a radially outward position, in which a zone of the plunger moves this tab radially out to unlock it, thereby freeing said needle-supporting part from said body.

In one possible embodiment of the invention, said means of keeping the container in position comprise:
- a flange formed at the opposite end of the container from the closed end of this container;
- engagement means integral with said plunger for connecting said flange to the plunger; and
- at least one tab comprising said engagement means and able to move in the radial direction of this plunger between a radially inward position, in which said engagement means connect said flange to the plunger, and a radially outward position, in which said engagement means are withdrawn radially wide of this flange, thereby releasing it.

The accompanying figures illustrate, by way of example, a preferred embodiment of the device according to the invention.

BRIEF DESCRIPTION OF THE DRAWINGS

FIG. 1 is a perspective view of the invention;

FIG. 2 is an exploded perspective view of the same, in a cross section passing along its axis;

DESCRIPTION OF THE PREFERRED EMBODIMENT

Figure 3:
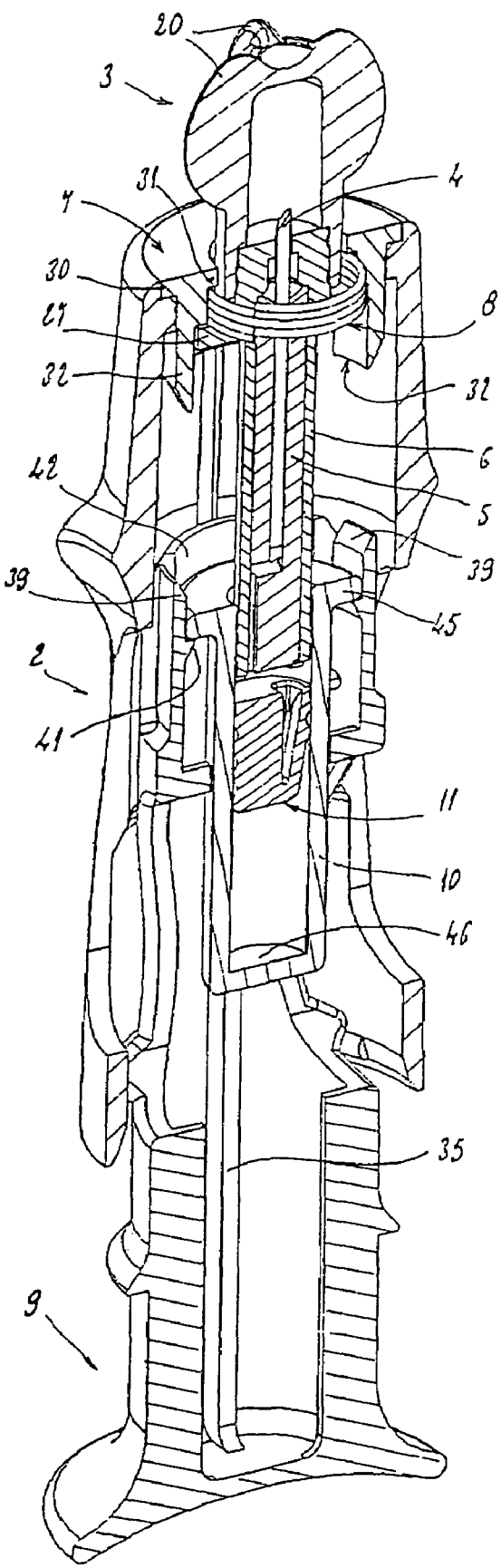
FIG. 3 is a perspective view of the same, in cross section passing along its axis, in the assembled condition.

The figures show a device 1 for injecting a product, particularly for medical use.

As is visible more particularly in FIG. 2, the device 1 comprises a body 2, a protective distal cap 3, a hollow injection needle 4, needle 4 assembly parts 5 to 7, a spring 8, a plunger 9, a container 10 and a piston 11, all described in detail below.

The body 2 is of a generally tubular shape and comprises a circular rib 15 near its distal end.

Figure 9:
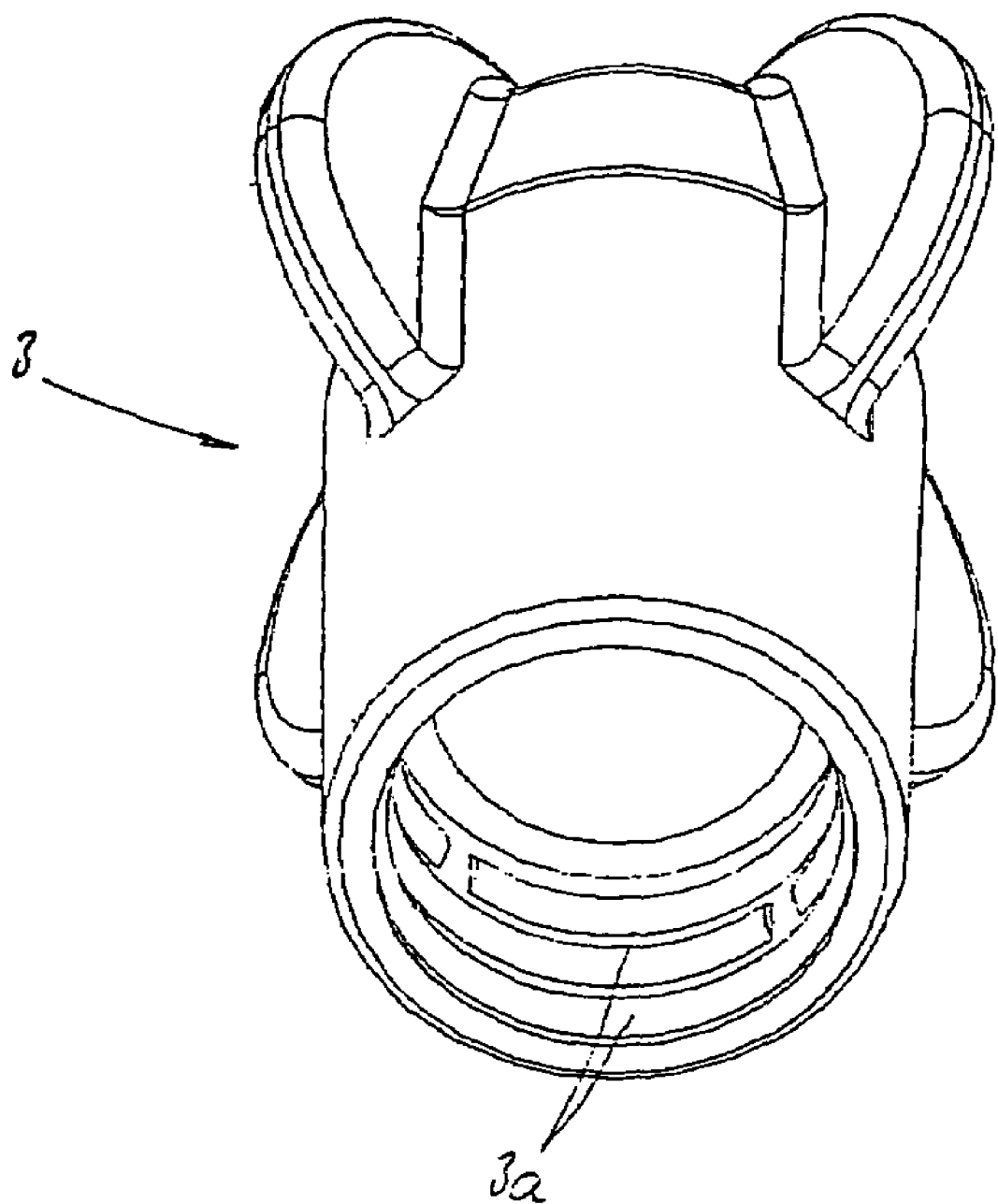
FIG. 9 shows, on an enlarged scale, a cap belonging to the device.

The cap 3 has wings 20 for holding it by and can be clipped onto a boss 21 formed by one of the needle 4 assembly parts 6 (needle-supporting part 6). As FIG. 9 shows, this cap 3 may include at least one opening for air to escape through when a portion 26 of the part 6 is inserted into the container 10, as will be seen later. In the embodiment shown in this FIG. 9, the cap 3 has several interrupted ribs 3a, tiered in the axial direction, with interruptions which are staggered angularly to form a maze.

The needle 4 is fixed to the part 5. The latter is generally cylindrical in shape and has a groove and a hole which form a flow channel communicating with the cavity inside the needle 4.

The part 6 has a tube-shape proximal portion 26 in which the part 5 is tightly housed, and comprises a distal hole to allow the needle 4 to be inserted through the boss 21. The portion 26 is designed to be inserted into the container 10, as mentioned earlier, and comprises a seal 25 near its proximal end. This portion 26 thus makes it possible to move the piston 11 inside the container 10 when the plunger 9 is moved relative to the body 2, as will be seen later.

The part 6 also includes a secondary flange 27 designed to clip into openings 28 (more particularly visible in FIG. 4) in two secondary tabs 29 belonging to the part 7. These tabs can move radially relative to the latter.

The part 7 is designed to fit tightly into the opening defined by the distal rib 15 of the body 2, while a distal flange 30 on the part 7 sits in the distal recess defined by this rib 15. This tight engagement secures the part 7 to the body 2.

The part 7 also includes an opening through which the boss 21 can pass so that the cap 3 can be placed on this boss. This opening is defined by a lip 31, the diameter of which is less than the diameter of the spring 8.

Figure 4:
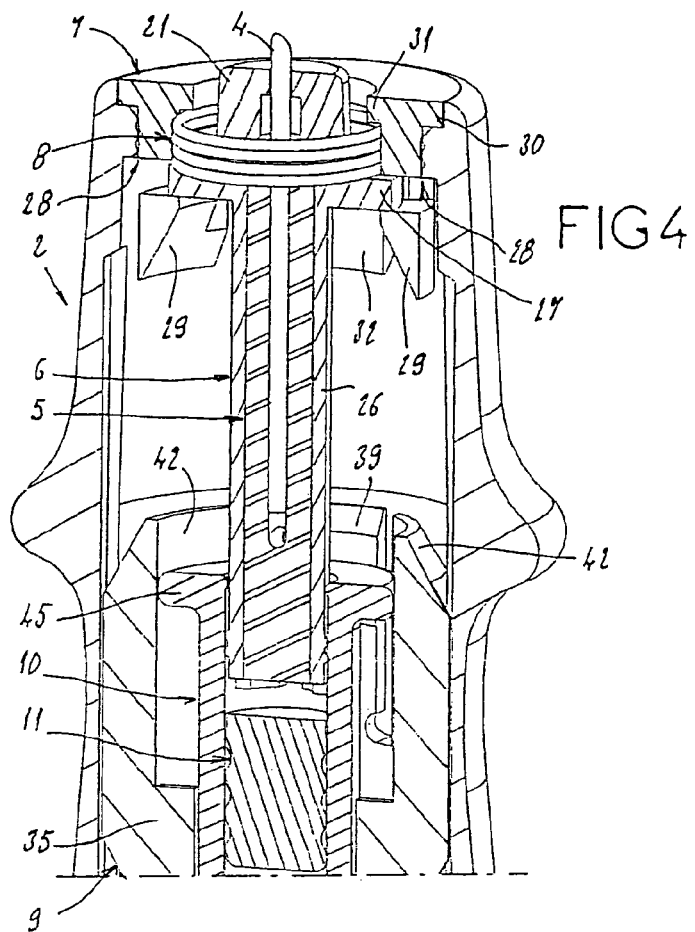
FIG. 4 is a partial view, on a larger scale, of its distal end, in cross section on a plane perpendicular to the cutting plane of FIGS. 2 and 3, with the needle kept in position by means belonging to this device.
Figure 5:
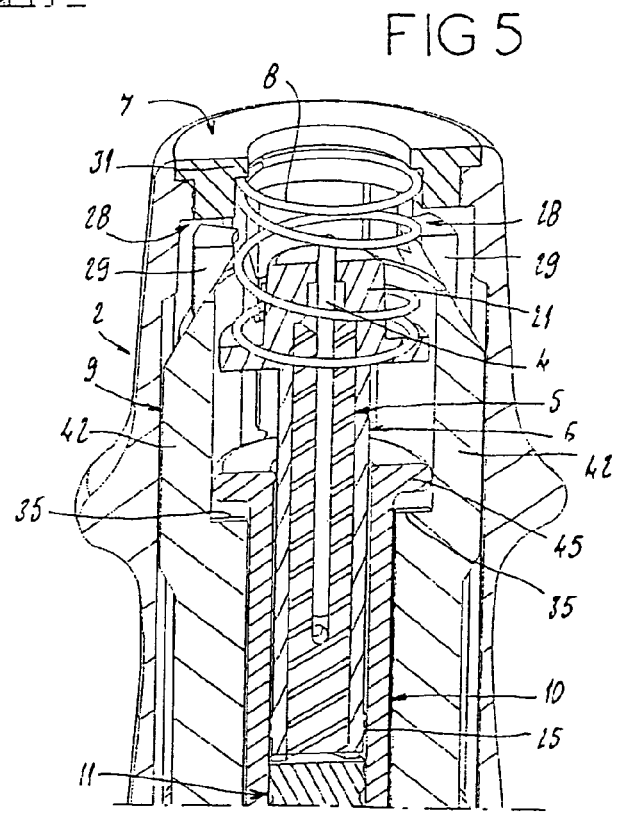
FIG. 5 is a view of the device similar to FIG. 4, in a relaxed position of these means of keeping the needle in position.

As shown in FIG. 4, this lip 31 keeps the spring 8 compressed between the proximal face of this lip 31 and the distal face of the flange 27 when the part 6 is clipped onto the part 7.

The part 7 also has walls 32 between the tabs 29. As can be seen in FIGS. 3 and 4, the tabs 29 have internal inclined ramps formed on their proximal ends while the walls 32 have external inclined ramps formed on their proximal ends.

The plunger 9 is engaged in the body 2 and can slide relative to the latter. It comprises lateral ribs 35 for guiding the sides of the container 10.

At its distal end, the plunger 9 forms two radially moveable tabs 39 with internal projections 41 forming stops for receiving a flange 45 on the container 10. When the flange 45 meets the projections 41, the flange 45 becomes connected to the plunger 9 in the direction in which the plunger 9 moves when performing the injection.

The plunger 9 also forms two walls 42 situated between the tabs 39. As can be seen in FIGS. 3 and 4, the tabs 39 comprise, at their distal ends, internal inclined ramps designed to interact with the ramps of the walls 32 at the end of the injection stroke, and the walls 42 comprise, at their distal ends, external inclined ramps designed to interact with the internal ramps on the tabs 29, likewise at the end of the injection stroke.

At the opposite end from the flange 45, the container 10 comprises a bottom 46. The injectable product is contained between the piston 11 and the walls of the container 10.

Figure 6:
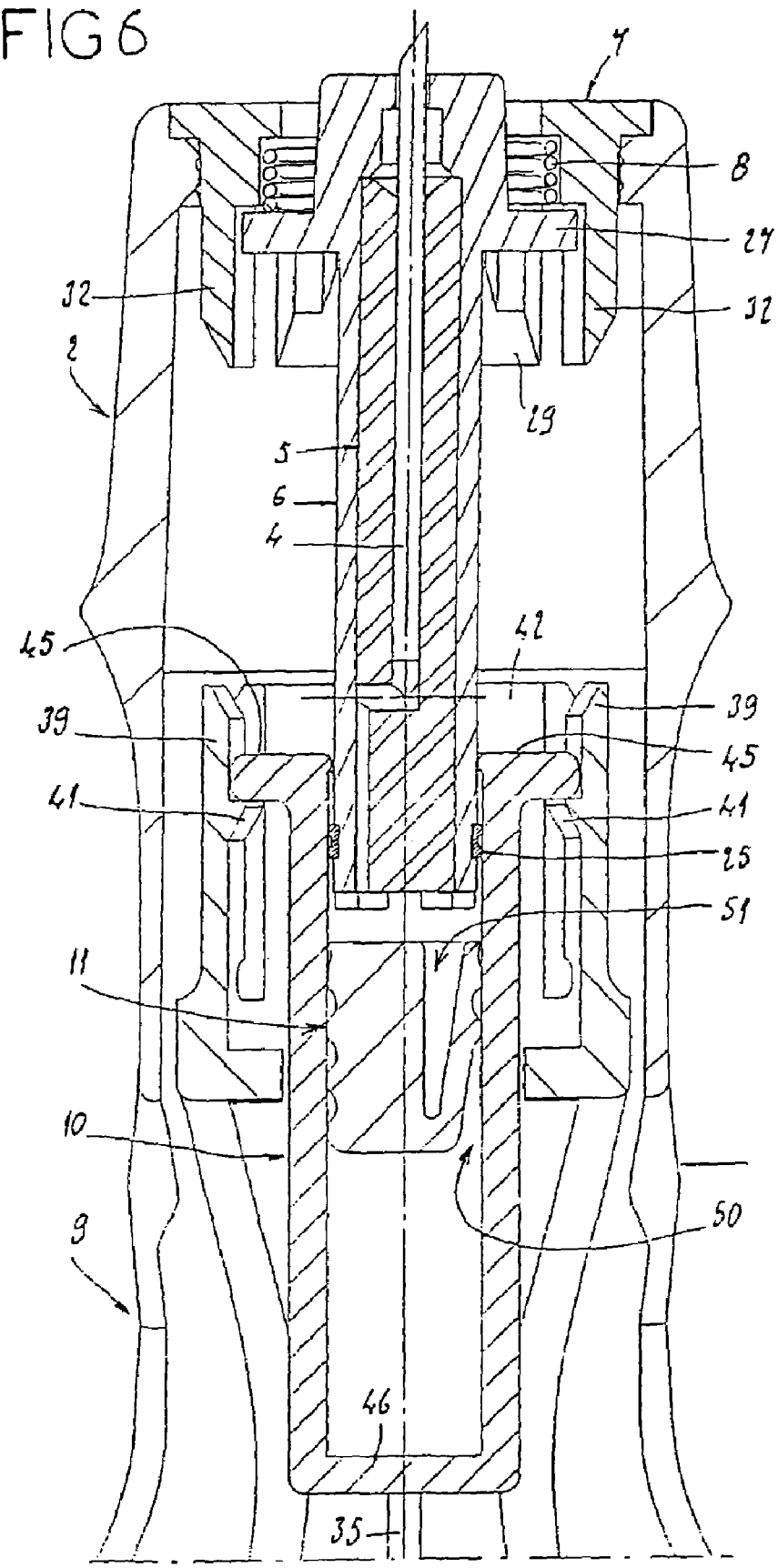
FIGS. 6-8 are partial views of the same, on a larger scale, in a cross section passing along its axis, respectively showing the storage position, the injection position and the end-of-injection position.

The piston 11 is made of a flexible material, especially an elastomer. It is of conical shape and is placed inside the container 10 so that its face having a smaller surface area is turned toward the injectable product. In this way, as FIG. 6 shows, it forms a gap 50 between itself and the wall of the container 10. The piston 11 also includes a lateral blind hole 51 running most of the way through its thickness, from its distal axial face, next to the side wall of the piston 11 defining said gap 50. The hole 51 is shaped so that it follows this side wall, at least approximately, and thus defines a peripheral zone occupying a portion of the periphery of the piston 11.

Figure 7:
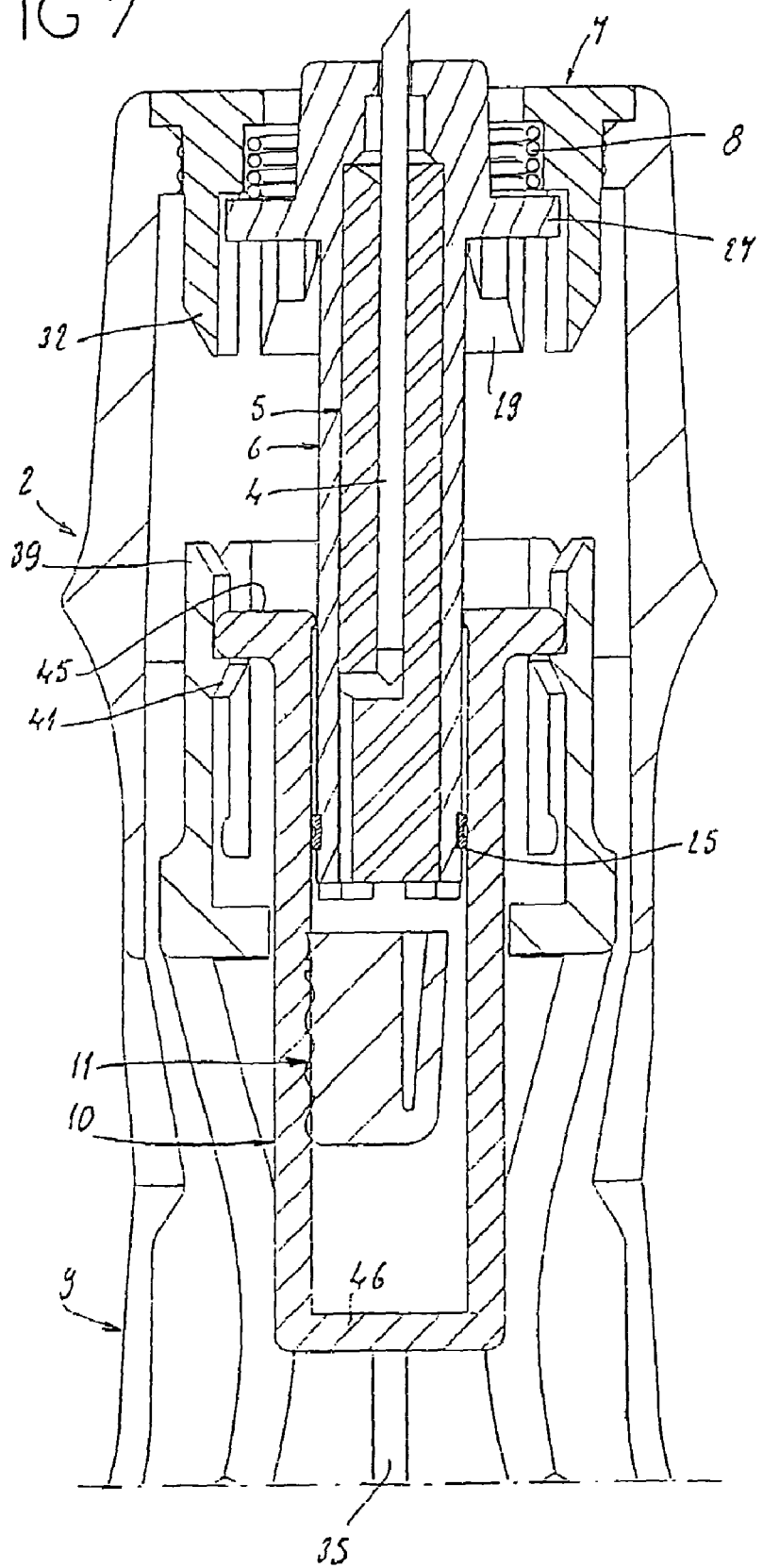

As a comparison of FIGS. 6 and 7 will show, this peripheral zone normally adopts a radially outward position shown in FIG. 6, in which it presses tightly against the wall of the container 10, and can adopt a radially inward position shown in FIG. 7, into which it withdraws under the pressure of the injectable product as the latter passes between the piston 11 and the container 10, due to the pressure of the piston 11 on the product, without the needle 4 piercing the piston 11. In the position shown in FIG. 7, the piston 11 is spaced from, and not in contiguous contact with, the needle 4.

In practice, the device 1 is initially in the storage position shown in FIG. 6, in which the flange 27 is in engagement with the tabs 29 and the flange 45 is kept in position by the projections 41. In this position the needle 4 projects beyond the distal end of the device to the desired depth for injection, which is an intradermal injection in the example illustrated.

The movement of the container 10 with the plunger 9 presses the piston 11 against the injectable product, which causes the product to flow between the piston 11 and the container 10, as appears in FIG. 7. The injection is then performed by continuing the movement of the plunger 9 relative to the body 2.

Figure 8:
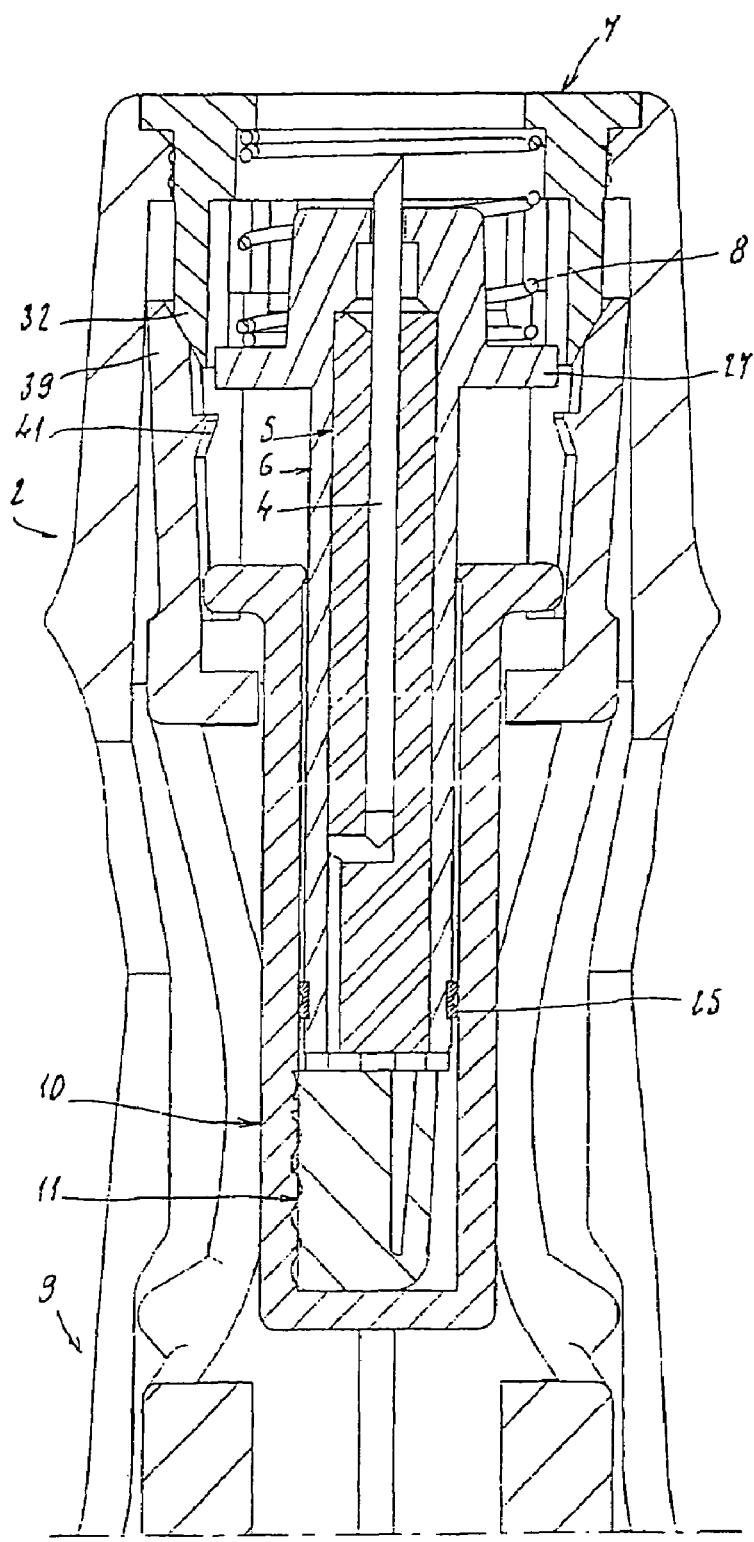

As the plunger reaches the end of the injection stroke, the ramps of the tabs 39 and of the walls 42 bear against the ramps of the walls 32 and of the tabs 29, respectively, with the result that the tabs 29 and 39 are displaced toward radially outward positions in which they free the flanges 27 and 45, respectively. The spring 8 can now relax, which causes a simultaneous retraction of the parts 5 and 6, and therefore of the needle 4, as well as of the container 10 owing to the friction of the seal 25, into a retracted position shown in FIG. 8. In this position the distal end of the needle 4 is behind the distal face of the part 7 and the flange 45 is behind the projections 41, on the proximal side.

It can be seen from the above that the invention makes a number of crucial improvements to the corresponding devices of the prior art, by making it totally proof against the risk of accidental stabbing which can occur after the injection.

It goes without saying that the invention is not limited to the embodiment described above by way of example, but that on the contrary it encompasses all alternative embodiments that come within the scope of protection defined by the claims appended hereto. In particular, the piston may comprise a pierceable zone located in line with the proximal end of the needle, this proximal end projecting from the proximal end of the part 5 in which it is held.

The invention claimed is:

1. A device for injecting a product, particularly for medical use, which comprises:
    a body housing a hollow injection needle and a container containing the injectable product; the needle is connected to the body but able to move relative to the latter between an injection position and a retracted position;
    a plunger that slides in the body and is displaceable relative to the latter to perform the injection; said container is closed at one end and is connected to this plunger but is able to move relative to the latter between a position that enables the injection to be performed and a retracted position;
    a piston engaged in the container and so shaped to have a blind hole located adjacent a peripheral portion, wherein, in a first configuration of the piston or relative position of this piston and of this container, it closes the container in such a way as to isolate the product from the environment outside this container and, in a second configuration of the piston or relative position of this piston and of this container, said peripheral portion of said piston is deflected into said blind hole so as to allow the product to pass between said piston and said container and out of the container without said piston being pierced, wherein the piston is spaced from, and not in contiguous contact with, the needle with the piston being in the second configuration or position;
    a flange formed at the opposite end of the container from the closed end of this container; and
    at least one tab able to move in the radial direction of the plunger between a radially inward position, in which said flange is connected to the plunger, and a radially outward position, in which said at least one tab is withdrawn radially wide of this flange, thereby releasing the flange.

2. The injection device as claimed in claim 1, which comprises a spring for moving the needle and the container to the retracted position without voluntary external action.

3. The injection device as claimed in claim 1, in which said body forms a distal end perpendicular to the axis of the needle, wherein the needle projects, in the injection position, from said distal end to a distance equal to the desired depth of insertion of this needle during the injection.

4. The injection device as claimed in claim 1, further comprising:
    a needle supporting part comprising a secondary flange, said needle being supported by said needle-supporting part; and
    at least one secondary tab able to engage with said secondary flange of said needle-supporting part, this at least one secondary tab being moveable radially between a normal, radially inward position, in which said at least one secondary tab engages with said secondary flange to keep said needle-supporting part in position relative to said body, and a radially outward position, in which the plunger moves said at least one secondary tab radially out to unlock the secondary flange, thereby freeing said needle-supporting part from said body.

* * * * *